US011490838B2

(12) United States Patent
Chamberlain et al.

(10) Patent No.: US 11,490,838 B2
(45) Date of Patent: Nov. 8, 2022

(54) SIMULTANEOUS MULTI-LED PULSE-OXIMETRY SAMPLING

(71) Applicant: Owlet Baby Care, Inc., Lehi, UT (US)

(72) Inventors: Caleb Chamberlain, Lehi, UT (US); Zack Bomsta, Provo, UT (US)

(73) Assignee: Owlet Baby Care, Inc., Lehi, UT (US)

( * ) Notice: Subject to any disclaimer, the term of this patent is extended or adjusted under 35 U.S.C. 154(b) by 399 days.

(21) Appl. No.: 16/732,676

(22) Filed: Jan. 2, 2020

(65) Prior Publication Data
US 2020/0214608 A1    Jul. 9, 2020

Related U.S. Application Data

(60) Provisional application No. 62/788,058, filed on Jan. 3, 2019.

(51) Int. Cl.
*A61B 5/1455* (2006.01)
*A61B 5/00* (2006.01)

(52) U.S. Cl.
CPC ........ *A61B 5/14552* (2013.01); *A61B 5/6829* (2013.01); *A61B 5/7214* (2013.01); *A61B 2562/0238* (2013.01); *A61B 2562/04* (2013.01)

(58) Field of Classification Search
CPC . A61B 5/0205; A61B 5/1455; A61B 5/14551; A61B 5/14552; A61B 5/14532; A61B 5/68; A61B 5/6801; A61B 5/6802; A61B 5/6813; A61B 5/6824; A61B 5/6825; A61B 5/6826; A61B 5/6829; A61B 2562/04; A61B 2562/0233; A61B 2562/0238
See application file for complete search history.

(56) References Cited

U.S. PATENT DOCUMENTS

| | | | |
|---|---|---|---|
| 4,407,290 A | 10/1983 | Wilber | |
| 4,800,885 A * | 1/1989 | Johnson | A61B 5/6826 356/41 |
| 4,807,630 A | 2/1989 | Malinouskas | |
| 5,424,545 A * | 6/1995 | Block | A61B 5/6826 250/341.7 |
| 6,711,424 B1 | 3/2004 | Fine et al. | |
| 6,778,923 B2 | 8/2004 | Norris et al. | |
| 8,108,022 B2 | 1/2012 | Balberg et al. | |
| 9,668,672 B2 | 6/2017 | Zalevsky et al. | |
| 2009/0259116 A1 | 10/2009 | Wasserman et al. | |

(Continued)

OTHER PUBLICATIONS

Kenneth Humphreys et al. "Noncontact simultaneous dual wavelength photoplethysmography: A further step toward noncontact pulse oximetry," *Review of Scientific Instruments* vol. 78, (2007) pp. 044304-1-044304-6.

*Primary Examiner* — Chu Chuan Liu
(74) *Attorney, Agent, or Firm* — Workman Nydegger

(57) ABSTRACT

A computer system for simultaneously sampling multiple light channels is configured to emit a first pulse-oximetry light signal from a first light source and to emit a second pulse-oximetry light signal from a second light source. The computer system then captures a combined pulse-oximetry signal from both the first pulse-oximetry light signal and the second pulse-oximetry light signal simultaneously at a photoreceptor sensor. The computer system identifies information within the combined pulse-oximetry signal, wherein the first light source and the second light source capture different attributes of the information.

8 Claims, 3 Drawing Sheets

(56) References Cited

U.S. PATENT DOCUMENTS

| | | | |
|---|---|---|---|
| 2009/0306487 A1* | 12/2009 | Crowe | A61B 5/14551 600/322 |
| 2010/0317937 A1* | 12/2010 | Kuhn | A61B 5/14552 600/323 |
| 2016/0345880 A1 | 12/2016 | Nakaji et al. | |

* cited by examiner

SIMULTANEOUS MULTI-LED PULSE-OXIMETRY SAMPLING

CROSS-REFERENCE TO RELATED APPLICATIONS

This application claims priority to and the benefit of U.S. Provisional Application Ser. No. 62/788,058 entitled "SIMULTANEOUS MULTI-LED PULSE-OXIMETRY SAMPLING", filed on Jan. 3, 2019, the entire content of which is incorporated by reference herein in its entirety.

BACKGROUND

The convergence of technology and medicine has led to stunning improvements in health and medical management. For example, MRIs, CAT scans, sonograms, and other related imaging technologies have provided medical researchers with previously unobtainable insight into the processes of the human body. Using these devices, doctors are able to diagnosis and treat a wide variety of diseases and conditions that previously were not treatable.

In addition to providing tools for medical practitioners, medical devices have increasingly become available to the public for personal use. For example, many wearable devices now include technology for tracking an individual's heart rate. One such technology that makes this possible is pulse oximetry. Pulse oximetry measures blood oxygen saturation (SpO2) by exposing the body to two or more wavelengths of light (e.g., red and infra-red). A computer processor then compares the difference in pulsatile amplitude at the two wavelengths.

Many conventional pulse oximetry devices utilize light sources, such as LEDs, and a photodiode to detect the light emitted by the light sources. When the optical paths from the photodiode to the two light sources is equivalent, and when ambient light doesn't change during sampling, this provides enough information to discern SpO2 with reasonable accuracy.

There is, however, a need in the field to increase the accuracy and efficiency of pulse-oximetry systems. In particular, pulse-oximetry systems that are used in mobile and/or power constrained configurations must deal with several unique challenges that do not arise in conventional hospital-based systems that typically have a non-limited power supply and a controlled operating environment.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

Disclosed embodiments include a system for simultaneously sampling multiple light channels. The system is configured to emit a first pulse-oximetry light signal from a first light source and to emit a second pulse-oximetry light signal from a second light source. The system then captures a combined pulse-oximetry signal from both the first pulse-oximetry light signal and the second pulse-oximetry light signal simultaneously at a photoreceptor sensor. The computer system identifies information within the combined pulse-oximetry signal, wherein the first light source and the second light source capture different attributes of the information.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings.

DETAILED DESCRIPTION

Typically, conventional pulse-oximetry sensors (also referred to herein as "pulse oximeters") sample two light sources within two separate "phases" that take place at different times, usually one after the other. In some cases, an ambient phase is also included. In the ambient phase, the light sources are turned off and the ambient light is measured by a photodiode (also referred to herein as "photoreceptor"). The measured ambient light can then be subtracted from the other measured phases. As such, in some embodiments, actual sampling may occur in three distinct phases.

Because the light measurements are taken at different times, the pathways between the light source(s) and the photoreceptor(s) can vary. For example, movement of the light sources and/or the photoreceptor can alter the pathway. Similarly, the amount of ambient light may change between the ambient-light-measurement phase and the other two light measuring phases. These changes in the pathways and ambient light levels between the sensor(s) and light source(s) reduce the reliability and accuracy of SpO2 estimates produced by the pulse-oximetry sensor.

Conventional strategies for mitigating against motion and ambient noise include reducing pulse width. However, the reduction of pulse width usually occurs at the expense of SNR. Additionally, some conventional systems mitigate against motion and ambient noise through post-processing of the pulse-oximetry data with complex and computationally expensive algorithms.

Figure 1:
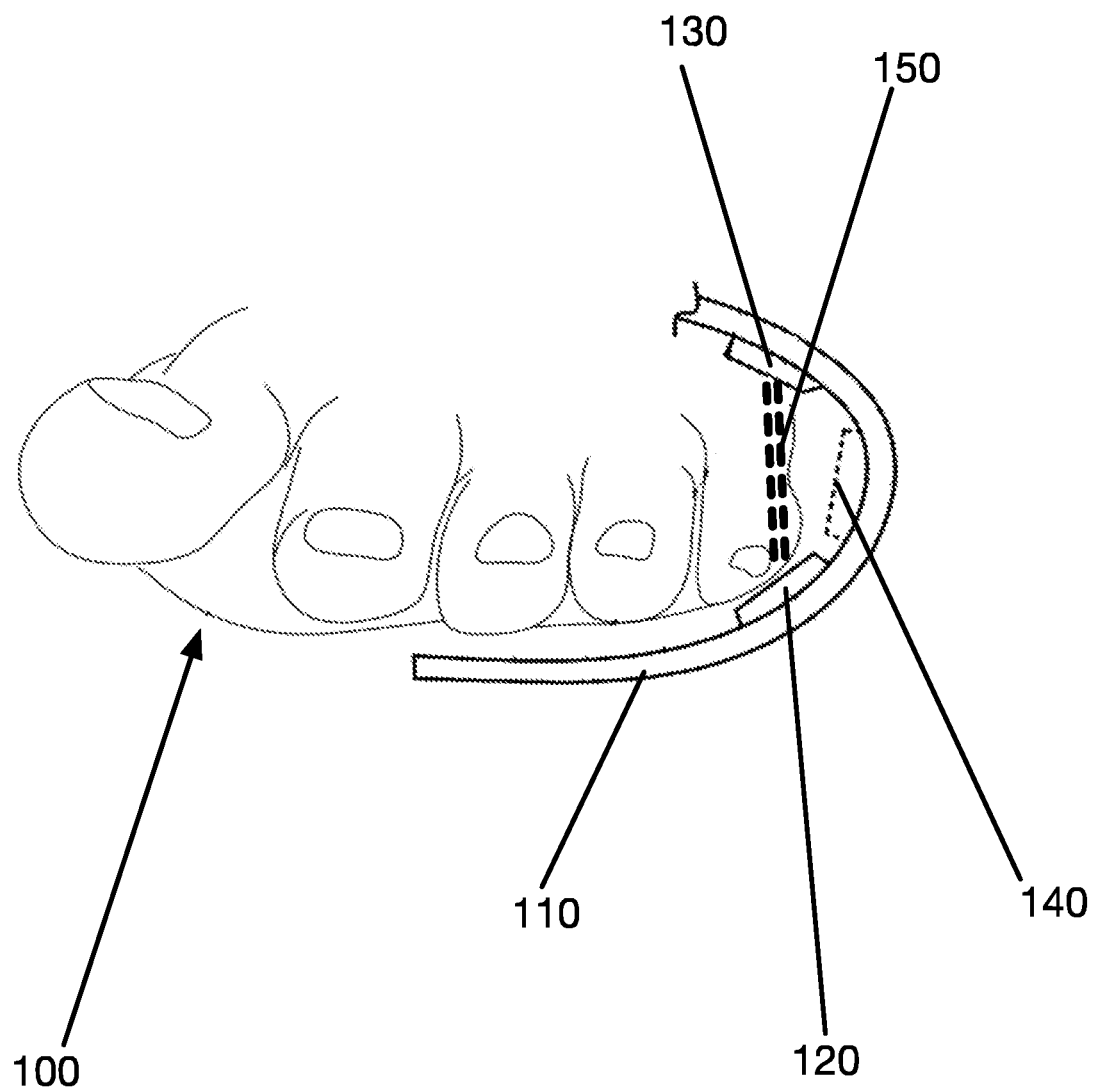
FIG. 1 illustrates an embodiment of a pulse-oximetry sensor on a human foot.

FIG. 1 illustrates an embodiment of a pulse-oximetry sensor 110 that drives and samples all light phases simultaneously. In the depicted embodiment, the pulse-oximetry sensor 110 is positioned on a human foot 100. One will appreciate, however, that a pulse-oximetry sensor 110 may take many physical forms and be positioned in a variety of different locations on a human body and still function as described herein.

In a transmissive embodiment, the pulse-oximetry sensor 110 comprises a light source 130 and a photodetector 120. Similarly, in a reflective embodiment, the pulse-oximetry sensor 110 comprises a light source 130 and a photodetector 140. In at least one embodiment, the light source 130 comprises multiple LEDs that are each capable of emitting different wavelengths of light. One will appreciate that the described photodetectors 120, 140 and the light source 130 are merely exemplary and could be otherwise arranged, depicted, joined, and/or configured.

In at least one embodiment, the light source 130 drives all light sources (e.g., red and infrared) simultaneously. Likewise, the photodetector 120 (or in the reflective case—photodetector 140) samples all light sources simultaneously. Because the sampling is performed simultaneously, time-varying paths and/or ambient light will affect all phases equivalently. One of skill in the art will appreciate that within conventional photodiodes it is difficult to isolate the effect of the multiple light sources. A photodiode is typically not capable of discerning between, for example, red and IR light. The photodiode only sees the sum of all light sources or, using an appropriate optical filter, it only sees one wavelength and not both.

Figure 2:
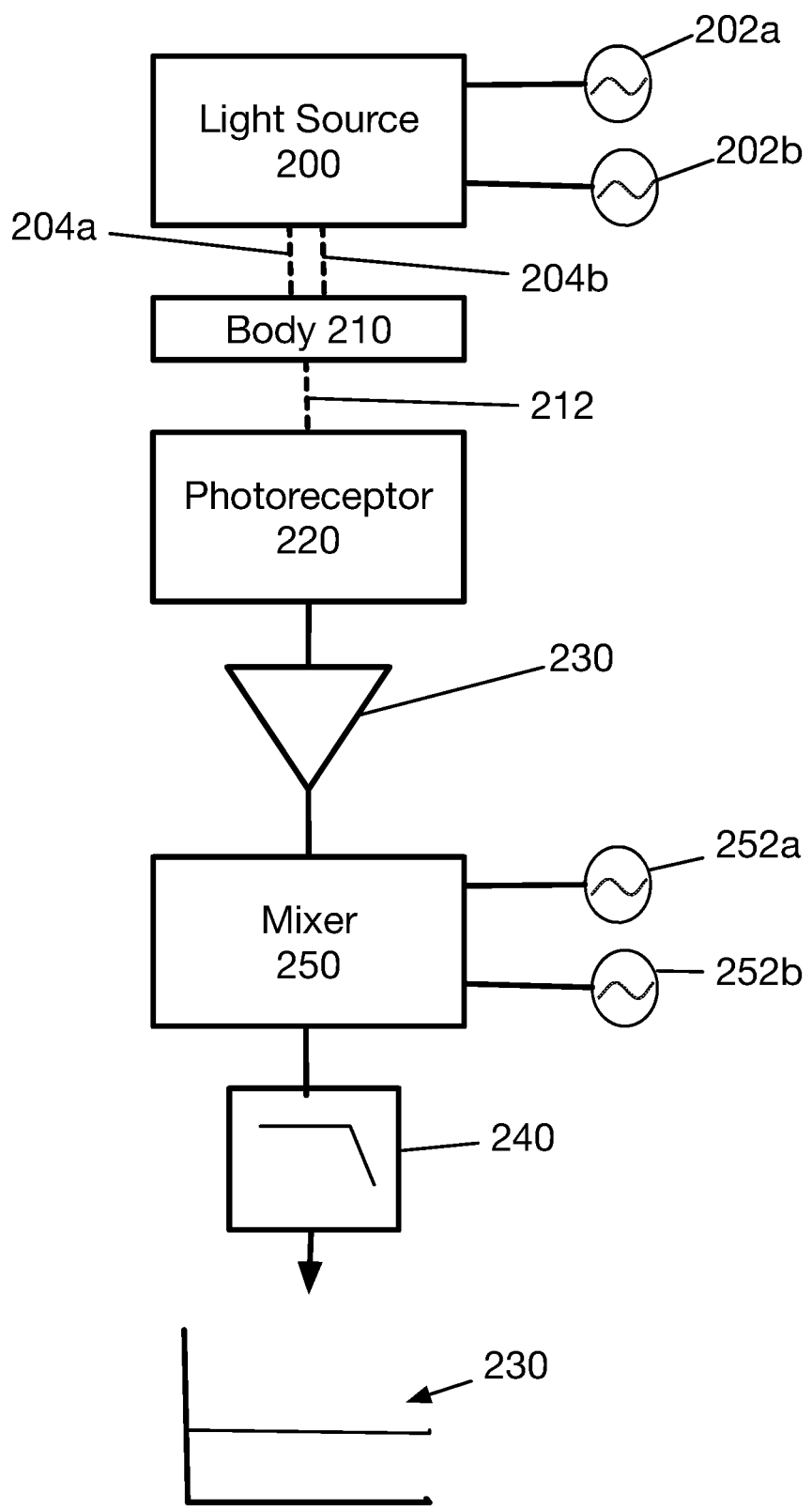
FIG. 2 illustrates an embodiment of a pulse-oximetry sensor system.

As depicted in FIG. 2, in at least one embodiment of a pulse-oximetry sensor, the light source 200 comprises two light sources, such as two LEDs, that are each driven at a high, unique carrier frequency 202a, 202b. As the light 204a, 204b from both light sources 200 passes through the body 210, the pulsatile waveform is effectively mixed with the carrier, like an amplitude modulated RF signal. The photoreceptor 220 receives the transmitted signal 212. The transmitted signal 212 is input into an amplifier 230. A mixer 250 within the pulse-oximetry sensor 110 mixes the amplified, transmitted signal with each carrier frequency or close intermediate frequencies 252a, 252b.

The pulse-oximetry sensor 100 then processes the received, mixed signal through a filter 240. The result is a DC or close-to-DC signal 230 that carries the information needed to determine SpO2. In the final, filtered signal, the ambient light is removed naturally by the mixing and filtering operations, as such, the ambient sampling phase is removed entirely. Additionally, because both light sources are active simultaneously, any changes in path length or ambient environment affect both light sources equivalently. In at least one embodiment, this disclosed method would work equally well for reflective and transmissive pulse oximetry.

Additionally, in at least one embodiment, the simultaneous sampling of the different light sources and the mixing of carrier waves allows for more aggressive filtering and the removal of aliasing problems.

Within conventional pulse-oximetry sensors, to save power and minimize artifacts from motion and ambient light, phase pulse widths are usually very short (e.g., on the order of 100 to 400 microseconds). The signal of interest (the pulsatile component) and its harmonics typically have a bandwidth of only ~13 Hz. Accordingly, normally, a low-pass filter would be applied with a corner frequency of 13 Hz, to remove all unwanted noise from the signal. An analog-to-digital converter (ADC) would then only need to sample at 26 Hz, or 52 Hz conservatively, to capture all information needed.

However, because the LEDs only turn on for a short period of time, such an aggressive filter is not an option. A 13 Hz low-pass filter has a time-constant of 12.2 milliseconds, so a pulse width of 100 to 400 microseconds does not give the filter enough time to settle. The result is that it is infeasible to filter at a low enough frequency to prevent aliasing, which increases noise and sensitivity to high frequency motion or ambient artifacts. This is true even of higher sampling rates, up to 1 kHz. Sampling even faster increases current consumption and decreases SNR because the LEDs must be active for longer and pulse widths must be even shorter to allow for more samples in a second.

In at least one embodiment disclosed herein, in the carrier/mixing method described above, the output of the mixers is a DC or close-to-DC signal. The amplitude of the DC or close-to-DC signal carries the pulsatile information. In this case, the on-time of the light sources is completely decoupled from the filters and the ADC. In the DC case (mixing to baseband), a 13 Hz filter can be applied, and the ADC needs only sample at 26 to 50 Hz, depending on how aggressive the analog filter is. Or, if desired, the sample rate and anti-aliasing filter corner can be increased, and more filtering can be applied digitally. In either case, aliasing can be avoided entirely because the sample rate is independent of the light source pulse rate and duty cycle.

In at least one additional or alternative embodiment, two filtered photodiodes and two light sources are utilized in an anti-parallel configuration for transmissive pulse-oximetry. For example, the pulse-oximetry sensor 110 of FIG. 1 may be used to describe this exemplary system. The pulse-oximetry sensor 110 comprises two photonics boards (e.g. 130, 120). The first photonics board 120 may comprise a red-light source and a photodiode with a visible light filter. The second photonics board 130 may comprise an IR-light source and a photodiode with an IR filter. Both the red and IR light sources engage simultaneously, shining in close to equivalent anti-parallel paths to their respective photodiodes. The photodiodes, with their optical filters, observe only the light of interest and ignore the rest. As such, the respective photodiodes are measuring the respective signals at the same time.

The following discussion now refers to a number of methods and method acts that may be performed. Although the method acts may be discussed in a certain order or illustrated in a flow chart as occurring in a particular order, no particular ordering is required unless specifically stated, or required because an act is dependent on another act being completed prior to the act being performed.

Figure 3:
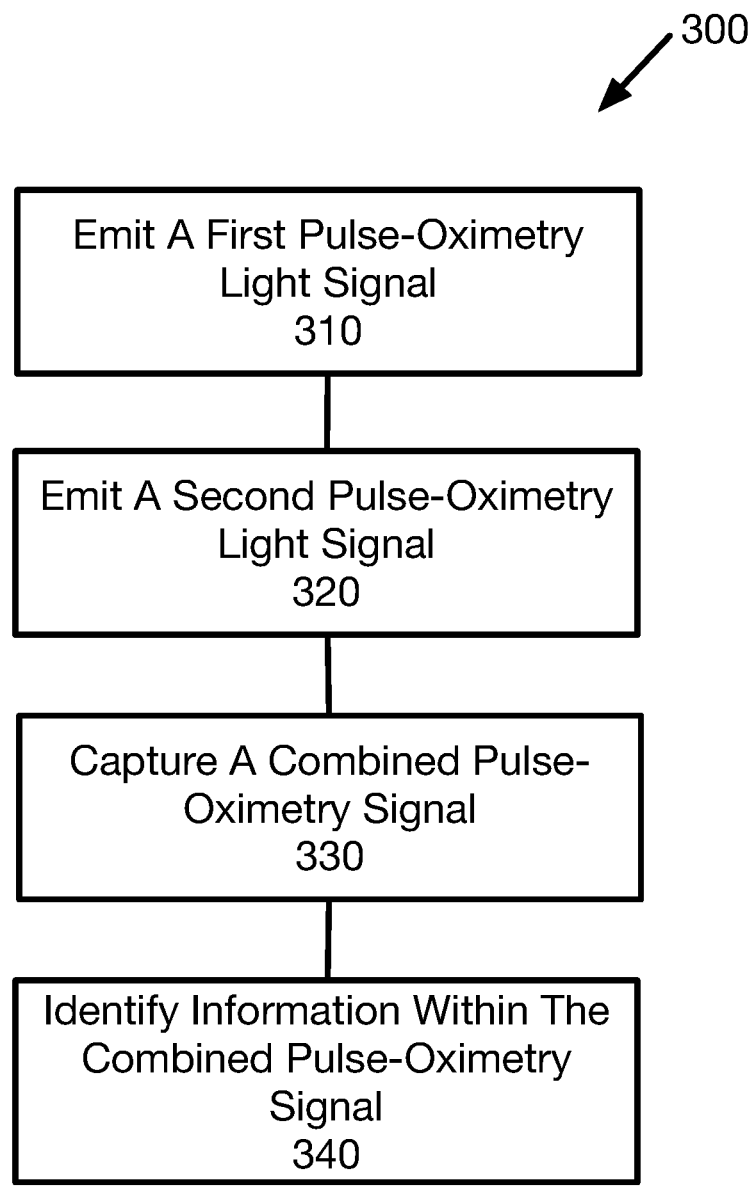
FIG. 3 illustrates a flowchart of steps in an embodiment of a method 300 for simultaneously sampling multiple light channels.

FIG. 3 illustrates a flowchart of steps in an embodiment of a method 300 for simultaneously sampling multiple light channels. The steps include an act 310 of emitting a first pulse-oximetry light signal from a first light source. For example, as depicted in FIG. 2, the light source 200 emits a first pulse-oximetry light signal 204a from a first light source. The first light source may comprise an LED that is embedded within the light source 200.

The method 300 also includes a step 320 of emitting a second pulse-oximetry light signal from a second light source. For example, as depicted in FIG. 2, the light source 200 emits a second pulse-oximetry light signal 204b from a second light source. The second light source may comprise an LED that is embedded within the light source 200.

Additionally, the method 300 includes a step 330 of capturing a combined pulse-oximetry signal from both the first pulse-oximetry light signal 204a and the second pulse-oximetry light signal 204b simultaneously at a photoreceptor sensor 220. For example, as depicted in FIG. 2, the photoreceptor 220 receives the transmitted signal 212 from the body 210. The transmitted signal comprises a pulsatile waveform that is effectively mixed with a carrier signal.

Further, the method 300 includes a step 340 of identifying information within the combined pulse-oximetry signal, wherein the first pulse-oximetry light source and the second pulse-oximetry light source capture different attributes of the information. For example, as depicted in FIG. 2, the pulse-oximetry sensor 110 generates a DC or almost DC signal 230. The amplitude of the DC or close-to-DC signal carries the pulsatile information, which is generated based upon initial variations in the first light signal 204a and the second light signal 204b as they pass through the body 210.

Accordingly, disclosure embodiments provide various benefits. For example, one possible benefit of the carrier/mixing method is that the architecture allows for a low power, low sample-rate ADC, combined with aggressive filtering, to reduce noise and mitigate against aliasing. In contrast, conventional off-the-shelf pulse-oximetry 3 suffer from aliasing problems due to rise-time constraints during sampling.

Further, the methods may be practiced by a computer system including one or more processors and computer-readable media such as computer memory. In particular, the computer memory may store computer-executable instructions that when executed by one or more processors cause various functions to be performed, such as the acts recited in the embodiments.

Computing system functionality can be enhanced by a computing systems' ability to be interconnected to other computing systems via network connections. Network connections may include, but are not limited to, connections via wired or wireless Ethernet, cellular connections, or even computer to computer connections through serial, parallel, USB, or other connections. The connections allow a computing system to access services at other computing systems and to quickly and efficiently receive application data from other computing systems.

Interconnection of computing systems has facilitated distributed computing systems, such as so-called "cloud" computing systems. In this description, "cloud computing" may be systems or resources for enabling ubiquitous, convenient, on-demand network access to a shared pool of configurable computing resources (e.g., networks, servers, storage, applications, services, etc.) that can be provisioned and released with reduced management effort or service provider interaction. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

Cloud and remote based service applications are prevalent. Such applications are hosted on public and private remote systems such as clouds and usually offer a set of web based services for communicating back and forth with clients.

Many computers are intended to be used by direct user interaction with the computer. As such, computers have input hardware and software user interfaces to facilitate user interaction. For example, a modern general purpose computer may include a keyboard, mouse, touchpad, camera, etc. for allowing a user to input data into the computer. In addition, various software user interfaces may be available.

Disclosed embodiments may comprise or utilize a special purpose or general-purpose computer including computer hardware, as discussed in greater detail below. Disclosed embodiments also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: physical computer-readable storage media and transmission computer-readable media.

Physical computer-readable storage media includes RAM, ROM, EEPROM, CD-ROM or other optical disk storage (such as CDs, DVDs, etc.), magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry program code in the form of computer-executable instructions or data structures and which can be accessed by a general purpose or special purpose computer. Combinations of the above are also included within the scope of computer-readable media.

Further, upon reaching various computer system components, program code means in the form of computer-executable instructions or data structures can be transferred automatically from transmission computer-readable media to physical computer-readable storage media (or vice versa). For example, computer-executable instructions or data structures received over a network or data link can be buffered in RANI within a network interface module (e.g., a "NIC"), and then eventually transferred to computer system RANI and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A computer system for simultaneously sampling multiple light channels, comprising:
   one or more processors; and
   one or more non-transitory computer-readable media having stored thereon executable instructions that when executed by the one or more processors configure the computer system to perform at least the following:
      emit, into a human body, a first pulse-oximetry light signal from a first light source, wherein the first light source is driven by a first carrier frequency;
      emit, into the human body, a second pulse-oximetry light signal from a second light source, wherein the second light source is driven by a second carrier frequency that is different from the first carrier frequency;
      after interacting with the human body, capture at a photoreceptor sensor a combined pulsatile signal that comprises information from both the first pulse-oximetry light signal and the second pulse-oximetry light signal;
      generate a mixed signal by mixing the combined pulsatile signal with the first carrier frequency and the second carrier frequency or close intermediate frequencies;
      generate a filtered signal by processing the mixed signal through a filter; and
      identify pulse-oximetry information within the filtered signal.

2. The computer system of claim 1, wherein the photoreceptor sensor comprises a single photodiode that captures both the first pulse-oximetry light signal and the second pulse-oximetry light signal simultaneously.

3. The computer system of claim 1, wherein the photoreceptor sensor comprises a first photodiode that captures the first pulse-oximetry light signal and a second photodiode that captures the second pulse-oximetry light signal simultaneously.

4. The computer system of claim 3, wherein the first photodiode comprises a first filter that is configured to exclude light other than the first pulse-oximetry light signal and a second filter that is configured to exclude light other than the second pulse-oximetry light signal.

5. A computer-implemented method for simultaneously sampling multiple light channels, the computer-implemented method implemented on one or more computer processors executing instructions stored on non-transitory computer-readable media, the method comprising:
   emitting, into a human body, a first pulse-oximetry light signal from a first light source, wherein the first light source is driven by a first carrier frequency;
   emitting, into the human body, a second pulse-oximetry light signal from a second light source, wherein the second light source is driven by a second carrier frequency that is different from the first carrier frequency;
   after interacting with the human body, capturing at a photoreceptor sensor a combined pulsatile signal that comprises information from both the first pulse-oximetry light signal and the second pulse-oximetry light signal;
   generating a mixed signal by mixing the combined pulsatile signal with the first carrier frequency and the second carrier frequency or close intermediate frequencies;
   generating a filtered signal by processing the mixed signal through a filter; and
   identifying pulse-oximetry information within the filtered signal.

6. The computer-implemented method of claim 5, wherein the photoreceptor sensor comprises a single photodiode that captures both the first pulse-oximetry light signal and the second pulse-oximetry light signal simultaneously.

7. The computer-implemented method of claim 5, wherein the photoreceptor sensor comprises a first photodiode that captures the first pulse-oximetry light signal and a second photodiode that captures the second pulse-oximetry light signal simultaneously.

8. The computer-implemented method of claim 7, wherein the first photodiode comprises a first filter that is configured to exclude light other than the first pulse-oximetry light signal and a second filter that is configured to exclude light other than the second pulse-oximetry light signal.

* * * * *